US00PP26469P2

(12) United States Plant Patent
Petryszyn

(10) Patent No.: US PP26,469 P2
(45) Date of Patent: Mar. 8, 2016

(54) ***HOSTA* PLANT NAMED 'COAST TO COAST'**

(50) Latin Name: ***Hosta* hybrid**
Varietal Denomination: Coast to Coast

(71) Applicant: Olga Petryszyn, Valparaiso, IN (US)

(72) Inventor: Olga Petryszyn, Valparaiso, IN (US)

( * ) Notice: Subject to any disclaimer, the term of this patent is extended or adjusted under 35 U.S.C. 154(b) by 146 days.

(21) Appl. No.: 13/999,435

(22) Filed: Feb. 25, 2014

(51) Int. Cl.
*A01H 5/12* (2006.01)

(52) U.S. Cl.
USPC ..... Plt./353

(58) Field of Classification Search
USPC ..... Plt./353
See application file for complete search history.

*Primary Examiner* — June Hwu

(57) ABSTRACT

A new and distinct *Hosta* plant named 'Coast to Coast' characterized by large, cordate, golden-yellow foliage, light lavender flowers beginning in early July on compact scapes just above foliage and upright habit.

1 Drawing Sheet

Botanical classification: *Hosta* hybrid (Tratt.).
Variety denomination: 'Coast to Coast'.

BACKGROUND AND ORIGIN OF THE PLANT

The present invention relates to a new and distinct *Hosta* plant, *Hosta* 'Coast to Coast' hereinafter also referred to as the new plant or just the cultivar name, 'Coast to Coast'. *Hosta* 'Coast to Coast' was hybridized by the inventor, Olga Petryszyn, in the June of 1998 in a trial garden at a personal *Hosta* garden in Chesterton, Ind., USA. The new plant originated from a breeding program conducted by the inventor with the specific intention to improve the garden worthiness and was later the subject of further trials in the inventor's garden in Chesterton, Ind. The female or seed parent was *Hosta* 'Manhattan' (not patented) and the male or pollen) parent was *Hosta* 'Golden Gate' (not patented). The new plant has been asexually propagated by division at the same garden in Chesterton, Ind. and also by careful whole shoot tip tissue culture propagation since 2011 with all resultant asexually propagated plants having retained all the same unique traits as the original plant. *Hosta* 'Coast to Coast' is stable and reproduces true to type in successive generations of asexual reproduction.

There are nearly 5,000 registered *Hostas* with The American *Hosta* Society, which is the International Cultivar Registration Authority for the genus *Hosta*. The most similar *Hosta* cultivars known to the applicant are the female and male parents. Other similar cultivars include *Hosta* 'Zounds' (not patented). Compared to 'Zounds' the instant cultivar has larger, more elongated and pointed leaves with a more glaucous underside, plant habit is more upright and larger, and the flower is more light lavender compared to the near-white flower of 'Zounds'. 'Coast to Coast' differs from the female patent, *Hosta* 'Manhattan', in that the new plant has more gold yellow foliage, the leaves are larger and the leaf margins are less undulated and flowers that are lavender compared to the purple of 'Manhattan'. In comparison to the male parent, *Hosta* 'Golden Gate', the new plant has more upright habit, heavier substance, lighter gold coloring and more rugose foliage with deeper pigmented flowers.

*Hosta* 'Coast to Coast' differs from all other *Hostas* known to the applicant, by the combination of the following traits:

1. Large, long, golden-yellow leaf blades with acute apexes, cordate bases and rugose upper surface;
2. Medium lavender buds opening to large lavender flowers beginning in early July in northern Indiana and effective for 3 weeks;
3. Numerous lavender flowers held close together and subtended by large lavender-pigmented bracts; and
4. Large upright habit.

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawing shows a ten-year old plant in peak flower in a shaded landscape in early summer at a trial garden in Chesterton, Ind.

DETAILED BOTANICAL DESCRIPTION

The following descriptions and color references are based on the 2001 edition of The Royal Horticultural Society Colour Chart except where common dictionary terms are used. The new plant, *Hosta* 'Coast to Coast', has not been observed under all possible environments. The phenotype may vary slightly with different environmental conditions, such as temperature, light, fertility, moisture and maturity levels, but without any change in the genotype. The following observations and size descriptions are of a ten-year old plant in a partially-shaded trial garden in Chesterton, Ind. with and supplemental water and fertilizer.

Botanical classification: *Hosta*×hybrid.

Parentage: Female (seed) parent is *Hosta* 'Manhattan'; male (pollen) parent is *Hosta* 'Golden Gate'.

Propagation: Division of the rhizome and sterile plant tissue culture.

Time to initiate roots from tissue culture: About two to three weeks.

Growth rate: Moderate to rapid.

Crop time: About 10 weeks to finish during the summer in a one-liter container from rooted tissue culture plantlet.

Rooting habit: Fleshy, lightly branching.

Root color: Nearest RHS 159C depending on soil type.

Plant shape and habit: Hardy herbaceous perennial with basal rosette of leaves emerging from rhizomes producing a radially symmetrical mound of mostly upright leaves becoming slightly rounded by late summer.

Plant size: Foliage height about 77 cm tall from soil line to the top of the leaves and about 125 cm wide at the widest point about 45 cm above soil line.

Foliage description: Entire, glabrous, slightly glaucous above becoming matte by mid-season, glaucous below and maintaining for the duration of the season.

Leaf blade: Blade margin sinuate; shape cordate, with broadly acute leaf apex and cordate auriculate base with overlapping lobes; proximal half of blade cupped or slightly folded to the center; average width to length ratio about 1:1.3; largest leaves about 35.0 cm long and 26.5 cm wide; average about 33.0 cm long and 25.0 cm wide.

Blade color: Adaxial (top) more yellow than RHS 145A, and lighter and more green than RHS 151A in regions with plenty of sunlight; in puckers and folds of leaf blade more yellow than RHS 137D; mid-season abaxial (bottom) between RHS 139C and RHS 138C.

Veins: 13 to 14 pairs of major parallel veins; impressed adaxial side; ridged abaxial side; color same as surrounding top and bottom leaf surfaces.

Petioles: Glabrous, entire margins, slightly glaucous on both adaxial and abaxial surfaces; conduplicate with margins curved toward center axis; about 1.4 cm wide and 30.5 cm long and about 7.0 mm deep.

Petiole color: Adaxial and abaxial margins lighter and more yellow than RHS 146D more green and more yellow than RHS 147D.

FLOWER DESCRIPTION

Flowers: Funnelform; single, perfect with two sets of three tepals; 42 to 54 per scape; tightly arranged with about 4 to 5 flowers per 1.0 cm centimeter of scape in some areas and spaced 2.5 cm apart in other areas, larger spacing usually only in lower portion of scape; normally each flower subtended by a single bract; first two to three flowers at or below foliage level; flowers about 5.5 cm wide and 7.0 cm long, (distal flowers smaller); remain open for a normal period, usually one to two days on plant or as cut stem; flower attitude horizontal to slightly drooping; flowers remain effective from early July into late-July for approximately three weeks in Chesterton, Ind.; no detectable fragrance.

Buds one to two days prior to opening: Oblate spheroid in outline with bluntly acute apex and basal two-fifths cylindrical; about 5.0 cm long; about 1.7 cm in diameter at widest point with basal two-fifths narrowing to about 4.0 mm diameter; distal buds smaller.

Bud color: One day from opening — light lavender between RHS 85D and RHS 76D; younger buds five days from opening — nearest RHS 85C.

Tepal: Glabrous; acute apex; margins entire; lobes elliptical with acute apex, approximately 5.5 cm long and 1.5 cm wide at widest point and fused in basal two-fifths; two identically sized and shaped sets of three fused in the basal one-half; inner set with adaxial margin about 3.0 mm wide of color near white, whiter than RHS 155D or RHS N155D and an outer clear margin of about 1.0 mm wide in the apical about 1.2 cm; inner set adaxial center about 8.0 mm with color nearest RHS 85C; outer set adaxial without distinct margin, color nearest RHS 85C across entire width; abaxial color of both sets between RHS 85D and RHS 91D; adaxial veins nearest RHS 85B and abaxial nearest RHS 91D; abaxial outer corolla tube nearest RHS 85C, adaxial corolla tube whiter than RHS 155D.

Pedicel: Approximately 8.0 mm long, 2.0 mm wide.

Pedicel color: Nearest RHS 137D with tinting of nearest RHS 79D.

Peduncle: Usually one per division, erect to about 1.2 mm diameter at base, average 92.0 cm tall; extending above foliage.

Peduncle color: Nearest RHS 147B developing tinting of RHS N186C in the upper regions where exposed to more light.

Gynoecium: Tri-carpeled.

*Style*.—Single, about 6.5 cm long, 1 mm diameter, curled upward at distal 1.0 cm; color lighter than RHS 155D.

*Stigma*.—1 mm to 2 mm in diameter; color lighter than RHS 155D.

*Ovary*.—Oval, about 5.5 mm long and 3.0 mm diameter; color between RHS 145A and RHS 145B.

Androecium: Six.

*Filaments*.—Six, about 1.0 mm in diameter and 6.0 cm long, curving upward the last 1.0 cm; color lighter than RHS 155D.

*Anthers*.—Oblong; dorsifixed, longitudinal; about 6.0 mm long and 2.0 mm wide, closest to RHS N187B.

*Pollen*.—Elliptical, less than 0.1 mm long; color nearest RHS 15A.

Bracts: Usually one or sometimes two before first flower then subtending normally one or rarely more flowers, glabrous, slightly glaucous adaxial and abaxial; entire margin, lanceolate, sessile, truncate, partly clasping, widest at base and tapering to acute apex; protruding upward and away from scape at about 75 degree angle from vertical and increasing to nearly 90 degrees in the last ⅓ of scape; lowest up to 5.0 cm long and 1.5 cm wide before first flower, progressively decreasing in both length and width distally.

Bract color: Abaxial and adaxial center portion nearest RHS 146C with margin region developing tinting of nearest RHS N187B on both adaxial and abaxial surfaces.

Fruit: Non-fleshy, dehiscent, many-seeded, tri-loculicidal capsule; oblong ellipse; about 3.5 cm long and 7.0 mm in diameter, color while maturing nearest RHS 146C and at dehiscence nearest RHS 161B.

Seed: About 30 per capsule; endospermic; flattened-elliptic wing surrounding embryo situated toward one end of ellipse; about 8.0 mm long and 3.0 mm wide and 1.0 mm thick at embryo; color nearest RHS 202A.

Disease and pest resistance and tolerance: The new plant has not shown resistance to diseases and pests beyond that common for *Hostas*. 'Coast to Coast' can tolerate more sun than typical *Hostas*. The plant grows best and shows best coloration with plenty of moisture, adequate drainage and light shade during the hottest period of the day, but is able to tolerate some drought when mature and direct sun without leaf burn when provided sufficient water. Hardiness at least from USDA zone 3 through 9, and other disease resistance and tolerance is typical of that of other *Hostas*. The new plant is useful for landscaping en masse, as a single specimen or small groups, and it is also useful for cut foliage or flower arrangements.

The invention claimed is:

1. A new and distinct ornamental plant cultivar named *Hosta* 'Coast to Coast' as herein described and illustrated.

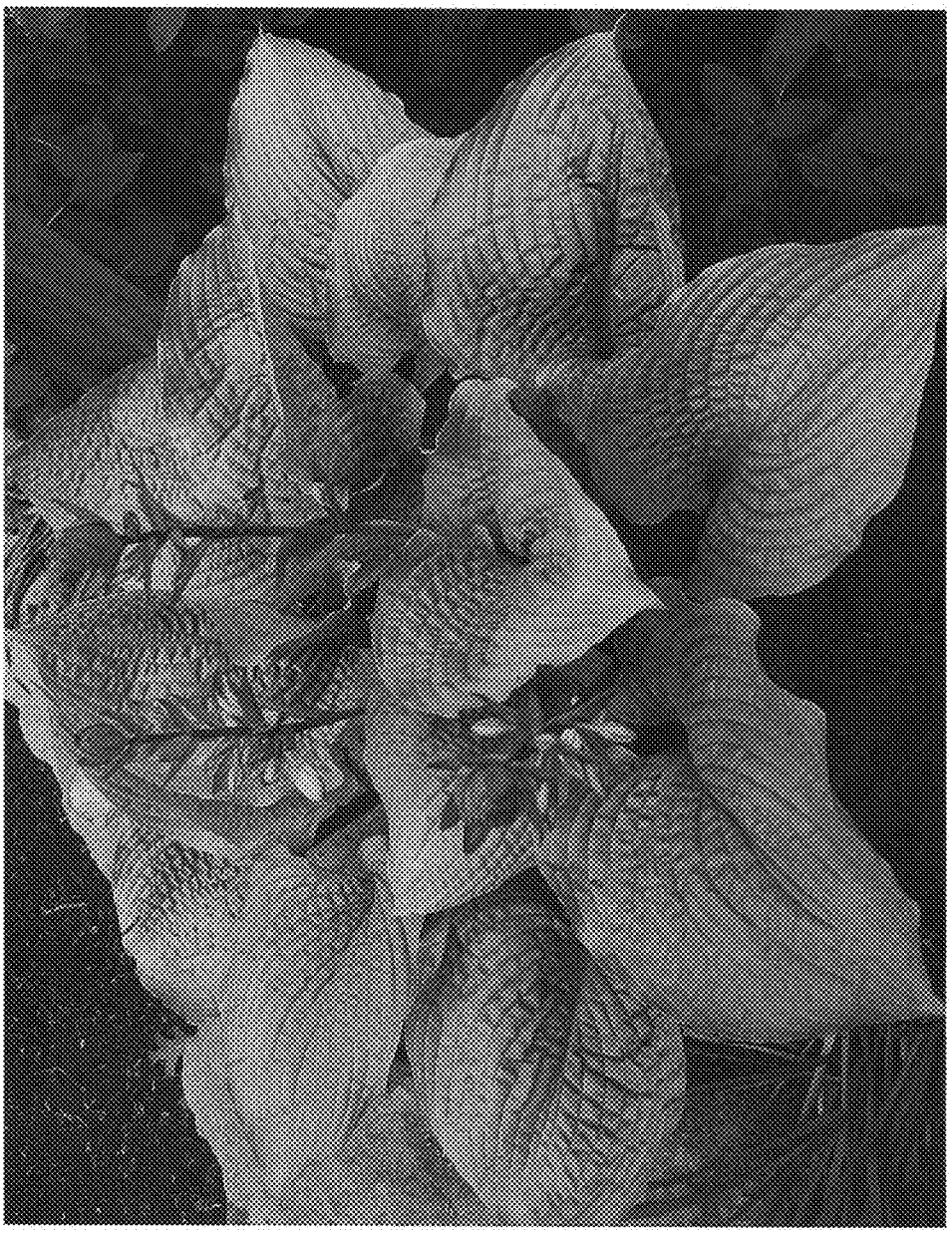

* * * * *